(12) United States Patent
Pasini et al.

(10) Patent No.: US 9,510,741 B2
(45) Date of Patent: Dec. 6, 2016

(54) MEDICAL CAMERA WITH SELECTION OF DIFFERENT WORKING MODES

(71) Applicants: Antonio Pasini, Imola (IT); Tommaso Virnicchi, Recanati (IT)

(72) Inventors: Antonio Pasini, Imola (IT); Tommaso Virnicchi, Recanati (IT)

(73) Assignee: CEFLA SOCIETÁ COOPERATIVA, Imola (BO) (IT)

( * ) Notice: Subject to any disclaimer, the term of this patent is extended or adjusted under 35 U.S.C. 154(b) by 616 days.

(21) Appl. No.: 13/973,180

(22) Filed: Aug. 22, 2013

(65) Prior Publication Data

US 2014/0055586 A1 Feb. 27, 2014

(30) Foreign Application Priority Data

Aug. 23, 2012 (IT) ................ BO2012A0451

(51) Int. Cl.
| | |
|---|---|
| *A61M 29/00* | (2006.01) |
| *A61F 5/04* | (2006.01) |
| *A61B 1/06* | (2006.01) |
| *A61B 1/00* | (2006.01) |
| *A61B 1/04* | (2006.01) |
| *H04N 7/18* | (2006.01) |
| *H02K 29/06* | (2006.01) |
| *G01B 11/02* | (2006.01) |
| *A61B 1/24* | (2006.01) |

(52) U.S. Cl.
CPC .............. *A61B 1/06* (2013.01); *A61B 1/00071* (2013.01); *A61B 1/00096* (2013.01); *A61B 1/00101* (2013.01); *A61B 1/00105* (2013.01); *A61B 1/00124* (2013.01); *A61B 1/00135* (2013.01); *A61B 1/00177* (2013.01); *A61B 1/00186* (2013.01); *A61B 1/00188* (2013.01); *A61B 1/0638* (2013.01); *A61B 1/0676* (2013.01); *A61B 1/0684* (2013.01); *A61B 1/24* (2013.01); *A61B 1/042* (2013.01)

(58) Field of Classification Search
CPC ........ H04N 5/225; H04N 7/18; H02K 29/06; A61B 1/04; A61B 1/24; A61C 3/00; G01B 11/02
See application file for complete search history.

(56) References Cited

U.S. PATENT DOCUMENTS

| | | | |
|---|---|---|---|
| 6,019,721 A | 2/2000 | Holmes | |
| 2002/0089672 A1* | 7/2002 | Noda ................ | G01B 11/161 356/505 |

(Continued)

FOREIGN PATENT DOCUMENTS

JP 2004329235 11/2004

*Primary Examiner* — Sath V Perungavoor
*Assistant Examiner* — Patricia I Young
(74) *Attorney, Agent, or Firm* — Themis Law

(57) ABSTRACT

A camera hand-piece for medical use includes a lighting system, an optical window, a fixed part in turn having an optical system for acquiring images through an optical window, an image sensor, electronic circuits for image processing, and optionally a prism. The hand-piece has an external part, which is mobile with respect to the internal fixed part, and rotatably commutable between at least two different working positions having different optical or lighting features, which are freely selectable by an operator. In one embodiment, the lighting system for lighting the framed field is positioned in the internal fixed part of the camera hand-piece, and the mobile distal part, non comprising electronic parts, can be sterilized in an autoclave.

14 Claims, 11 Drawing Sheets

(56) References Cited

U.S. PATENT DOCUMENTS

| | | | |
|---|---|---|---|
| 2005/0003323 A1* | 1/2005 | Katsuda | A61B 1/00089 433/29 |
| 2005/0014996 A1* | 1/2005 | Konomura | G02B 23/2476 600/175 |
| 2005/0068444 A1 | 3/2005 | Oshima | |
| 2009/0203965 A1* | 8/2009 | Fujiyama | A61B 1/00096 600/130 |
| 2011/0134234 A1 | 6/2011 | Kim | |
| 2012/0281135 A1* | 11/2012 | Gebhardt | A61B 1/042 348/374 |

* cited by examiner

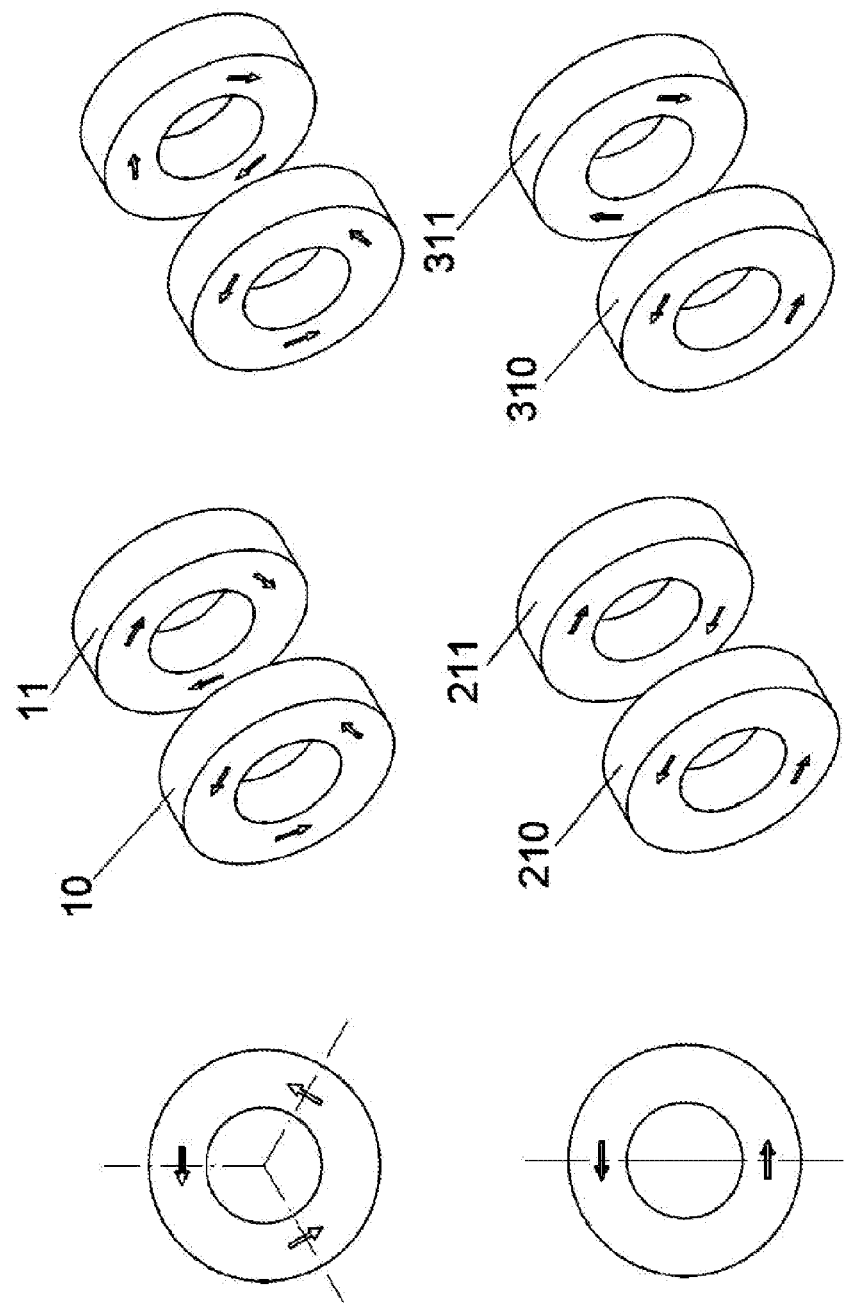

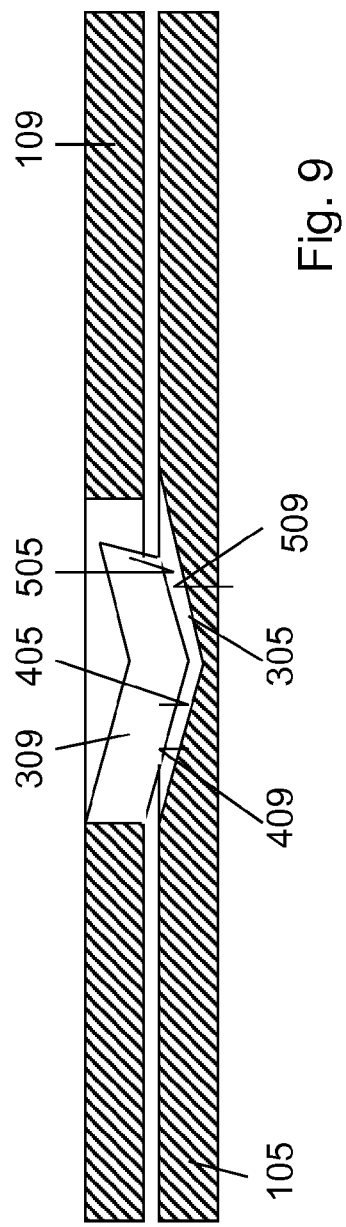
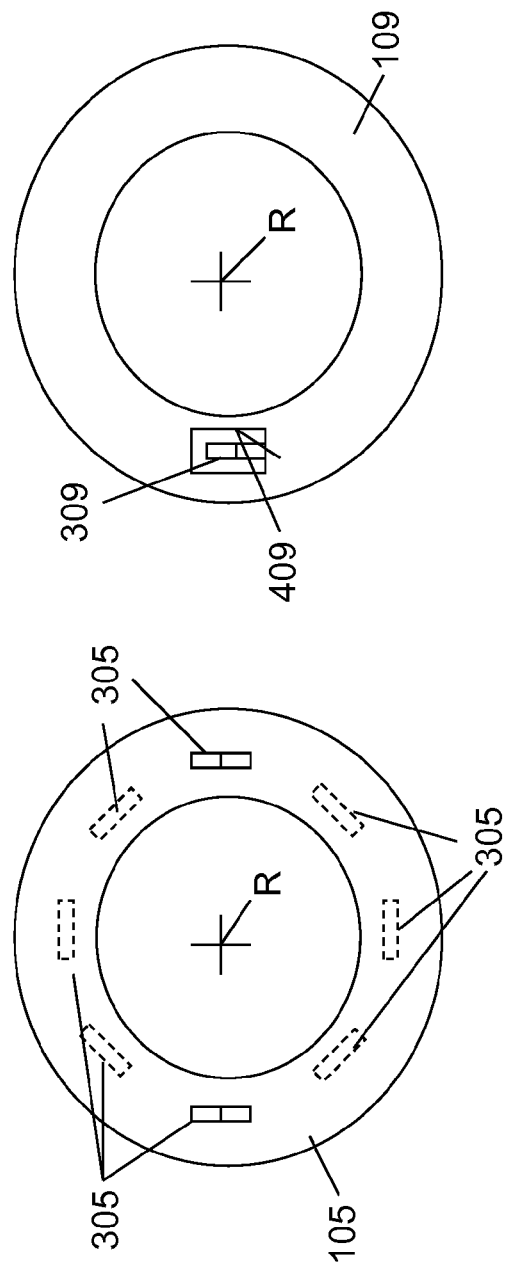
Fig. 9
Fig. 10
Fig. 11

MEDICAL CAMERA WITH SELECTION OF DIFFERENT WORKING MODES

FIELD OF THE INVENTION

The present invention relates to a camera for medical use, in particular to an intraoral camera having a system for configuring it to different optical working modes.

BACKGROUND OF THE INVENTION

It is known to use vision systems based on cameras in medical practice, under the form of both cameras adapted to endoscopes and cameras specifically designed for the vision of specific areas of interest, e.g. intraoral cameras, colposcopes, or various kind of endoscopes, even for surgical use.

Historically, cameras utilized in medical practice used to comprise an optical system, often of elongated form; a device for capturing images, typically a CCD or CMOS sensor; and electronic circuits for acquiring and processing images in the form of video signals, suitable for connecting to a video screen or to a personal computer for saving the video sequence or single frames. Such cameras traditionally needed to be connected to a cable for carrying a power supply to the camera and video signals to a display screen for viewing images.

Also known are cameras used in medical practice, which are provided with a lighting system using lamps or Light Emitting Diodes (LEDs), emitting both white light for normal vision, and specific wavelengths, e.g. infrared or ultraviolet. The different wavelengths have the aim of facilitating diagnosis of particular pathologies, like mycosis in the case of cameras designed for dermatology, or the presence of plaque, caries or pathogens in the case of intraoral cameras, or cancerous or pre-cancerous lesions in the case of colposcopes and endoscopes.

Cameras used in medical practice can optionally be provided with a focusing system, for a better vision of objects lying at different distances; otherwise, cameras can be pre-set in an optimal focusing condition based on the use for which they are designed.

Therefore, medical cameras of different types are known, but until today many of the products available on the market have poor or no use flexibility. In particular, when conditions requiring the variation of the working mode of the camera arise, the use of the same camera during clinical use can be impossible or very uncomfortable for the operator.

For instance, when an operator is working with white light for vision in the visible spectrum, the need may arise to illuminate an anatomic portion with a light having a different specific wavelength, useful to detect specific pathologies.

Otherwise, in some cases there are vision difficulties, due to a pre-set focus that does not correspond to the needs of a specific clinical practice.

Document US2011/0134234 discloses an electronic microscope, which includes a handle having an outer body enclosing a main body, and an image sensor such as a CMOS or CCD sensor, in which an image memory, a tact switch, and a USB port are mounted on the main board. A lens controller is fixed to the front end of the outer body of the handle and includes an inner case having a guide slot in the circumference and a flange on one end to which the handle is coupled. An outer case is rotatably coupled with the inner case from outside and has a spiral passage, such as a spiral hole or a spiral groove, in the circumference communicating with the guide slot. A lens unit is inserted into the inner case and has a guide rod inserted into the guide slot and into the spiral passage such that the lens unit moves back and forth in response to rotation of the outer case. A light guide coupled to the front end of the lens controller includes a LED board with a LED radially mounted on the LED board, and an observation filter detachably provided on the front end of the lens controller, in which the observation filter has a conical shape with the diameter decreasing toward the front end thereof, and observes body regions including the skin, scalp, nose, mouth, ears, and acupuncture spots in the ears. The lens controller includes a main case covering the outer circumference of the outer case and a focus adjustor provided on one end of the outer case, in which the focus adjustor rotates the outer case from outside, so that the lens unit can be precisely adjusted.

This device allows a continuous adjustment of the focus of the lens unit by rotating a focus adjustment member in the form of a ring. This device has a very complex construction, which renders it non suitable for endocavitary use, due to difficulties in substituting and/or sterilizing the parts that come into contact with the anatomical cavities of different patients.

Moreover, that continuous adjustment renders the device difficult to use because it requires several adjustments before reaching the right focus for a specific operative condition, and the user needs to operate the adjustments of the focus with both hands. Thus focus adjustment requires several actions of inserting the device in the cavity, controlling the image focus on the display, and if not correct, extracting the device from the cavity, making a first adjustment and then reintroducing the device in the cavity and controlling the new focus. If the adjustment is not sufficient for a desired image quality, the above steps must be repeated until the image desired image quality has been achieved.

Furthermore, if changes in the type of illumination and or in the settings of the CCD or CMOS parameters and/or of the processing unit generating the image or video data from the received signals must be performed, this must be done by physically changing the illumination source or by adding filters and by inputting new operative parameters and settings for the processing unit through control interfaces.

SUMMARY OF THE INVENTION

An object of the present invention is providing a camera for medical use, designed for communicating with the patient, for clinical diagnosis or for surgical practice, wherein switching from one working mode to another is easy, for example from lighting with visible light to lighting with a pre-set wavelength, without the above mentioned disadvantages, and with a construction that is simple and economic.

This object is achieved by a medical camera having the features described hereinafter. Advantageous embodiments and refinements are also described hereinafter.

A device according to the present invention is different from all the known devices at least because it can switch camera operation between at least two different working modes, providing for a simpler use of the camera, closer to the needs of an operator.

In one embodiment, at least the mobile part of the camera is formed by a sleeve shaped cap which is rotatably supported on a distal section of a fixed part of a hand-piece, which fits inside the mobile part around one axis coinciding with the longitudinal axis of the mobile part or of the distal section of the fixed part, or parallel to one of those axes. The distal section of the fixed part carries the optical system. The at least two optical windows are mounted at the distal end of the mobile part at different angular positions one with respect to the other along a circumferential path relatively to the rotation axis coinciding with the light input of the optical system, so that by rotating the mobile part each of the at least two optical windows can be alternatively brought into the light path of the optical system.

In combination or alternatively to the above, on the mobile part two or more different lighting systems emitting light with different frequency spectra and/or with different intensity and/or with different apertures of the emitted light, are mounted each one in a different angular position with respect to the other along the outer surface of the mobile part, in particular at the distal end and in non axial coincidence with the optical windows. By rotating the mobile part each one of the light systems can be brought into an operative condition, that is, in a position relative to the fixed part and the optical system, in which the irradiated light is directed to the region to be imaged and against which the optical system is also directed. By providing electric contacts on the fixed part, which are connected to a source for a driving signal of the lighting system, and by providing for each lighting system electric sliding contacts on the mobile part, it is possible to automatically connect to the driving source the lighting system, which is respectively brought in the working position, while the at least one additional lighting system is not fed with the driving signal. In this case the contacts on the mobile part and on the fixed part are positioned one in relation to the other that the sliding contacts of the mobile part connected to one of the lighting systems will be coincident and in touch with the corresponding electric contacts on the fixed part when the mobile part has the relative angular position with respect to the fixed part corresponding to the working position, in which the lighting system is to be active.

In one embodiment, the means for determining the relative angular position of the mobile part with respect to the fixed part are the sliding contacts for feeding the driving signal.

Several options are possible which provide, for example, sensing the power absorption of the currently activated lighting system and determining from this value the kind of lighting system that is activated.

In another embodiment, the information about which light system is activated can be used as information for also setting the electronic processing unit according to the specific kind of lighting system in use.

More generally, in one embodiment, the means for sensing the relative angular positions and generating a different control signal corresponding to each one of at least two different discrete relative angular positions for automatically changing the values of the optical parameter and/or the driving parameters of the lighting system and/or the settings of the electronic circuits for image processing according to predefined values and settings univocally correlated to each one of the discrete relative angular positions of the mobile part and of the fixed part can be any kind of coding means of the angular positions of the mobile part, the coding means comprising a unit for generating an angular position identification code and means for reading or receiving said code. A person of skill in the art can appreciate the type of coding means to select among those known in the art.

The signals generated by the sensing means and univocally associated each one to a specific angular position of the mobile part can be used for changing each of the working parameters or settings of an intraoral camera, alternatively or in any combination and sub-combination, and particularly alternatively or in combination or sub-combination with each of the optical, lighting and/or processing unit parameters or settings.

In one embodiment, the code can be generated by an array of sensing contacts provided on the fixed part in a certain angular position relative to the axis of rotation and an array of coding contacts for each working position of the mobile part. The array of coding contacts on the mobile part cooperates alternatively with the sensing contact on the fixed part, and each of the coding arrays on the mobile part have a different pattern, or the contacts cab be connected together according to different connection schemes for each of the corresponding working positions, thus forming a univocal identification code for each of the working positions, i.e. for the corresponding relative angular position of the mobile part and the fixed part. Such univocal identification code is read by the electronic processing unit connected with the array of sensing contacts on the mobile part, and is then interpreted as a control signal for changing the settings according to the selected working position.

Other embodiments are disclosed in the detailed description that follows.

It should be noted that this arrangement provides not only for a change in lighting and/or optical features of the camera by simply rotating the mobile part in relation to the fixed part, but also for setting a specific working position the entire set of parameters for performing the processing of the signal into a video, or updating an image to be optimized with the optical and/or lighting features of the selected working condition.

Another feature, which helps in providing more reliability and in facilitating the adjustment of the mobile part relative to the fixed part at each working position, includes having means that releasably block the mobile part relative to the fixed part at each respective angular position corresponding to a working position. These means are set to generate a releasable blocking force whose intensity is set at a level that can be overcome by exercising a light manual rotational action on the mobile part relative to the fixed part.

Several ways of performing this task are available to a person of skill in the art, among which are mechanical blocking means consisting in elastically biased locking means. In one embodiment, these means comprise at least one tooth or protuberance having a rounded or chamfered end, which is mounted in a seat in the mobile or fixed part, sliding backward and forward in the direction of a facing surface of respectively the fixed part or the mobile part, and one locking notch for each working position having a fixed angular position, the notches being provided along a circumferential path around the axis of rotation which coincides with a circumferential path around the axis of rotation, on which the locking notch is provided.

Alternative means for temporarily and releasably locking the mobile part to the fixed part in each of the working positions may consist in magnetic means, which are disclosed with more detail hereinafter.

According to a possible variant of the above embodiments, the different light systems may be provided on the fixed part, and more precisely at the distal part of the fixed part covered by the mobile part. In this case no sliding contacts are needed on the mobile part and the means for sensing the relative angular position of the mobile part to the fixed part may be simple RFID tags positioned on the mobile part along a specific circumferential path relatively to the axis of rotation and of one or more RFID reading tags, which are positioned on the fixed part. This embodiment has the advantage of allowing an easy separation of the mobile part from the fixed part and carrying out a sterilization of it or providing a kit of parts comprising a fixed part to which two or more differently shaped or equipped mobile part may be alternatively associated. Each of the mobile part is provided with optical windows and optical or other organs optimized for different tasks.

Furthermore, in relation to the above variant, at least two lighting systems may be provided on the fixed part, which are coincident with an optical windows on the mobile part, while the at least two lighting systems are activated alternatively one in relation to the other depending on the angular position of the mobile part relative to the fixed part. According to this variant, the angular position signals generated by the sensing means of the angular position of the mobile part relative to the fixed part are the control signals for switching the feeding signals to the lighting system to be activated according to the selected angular position of the mobile part.

Relating to the definition of the terms "optical parameter" or "parameters of the optical system," these terms mean any optical effect of an optical active element provided in the light path, such as passing bandwidth of filters, deflecting or collecting effects of lenses for concentrating or enlarging the illuminated area, for shifting the area, or for changing the focus of the optical system. Other parameters may include a polarization effect.

In regard to the "settings" of the electronic processing circuit, this term indicates any parameter commonly known in relation to the transformation of CCD or CMOS signals in image frames or video, such as, for example, frame rate, or RGB or YUV or CMY color gains matrix settings for optimizing the processed image with the frequency spectrum of the light used.

In the following description, embodiments of an intraoral camera will be discussed without losing generality.

BRIEF DESCRIPTION OF THE DRAWINGS

The present invention will be now described with reference to the enclosed drawings, showing different non-limiting embodiments.

FIG. 3 Details of the magnetic rings in prospective views;

FIGS. 9 to 11 A first embodiment of mechanical releasable blocking means of the mobile part relative to the fixed part in different relative angular positions, each coinciding with a different setting of optical and/or lighting and/or processing parameters;

DETAILED DESCRIPTION OF EMBODIMENTS OF THE INVENTION

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Figure 1:
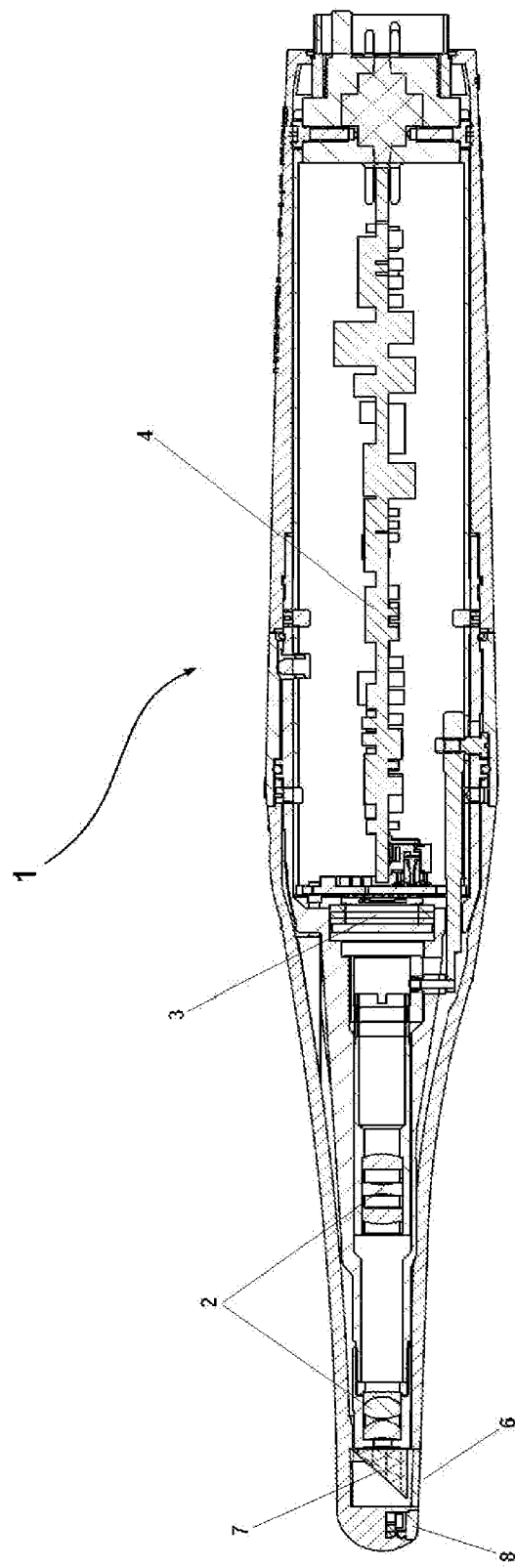
FIG. 1 Schematic longitudinal section view of a prior art camera, of intraoral type.

With reference to FIG. 1, showing a typical intraoral camera of known type, reference number 1 indicates a camera hand-piece in its entirety, which comprises:

an optical system 2;

an image sensor 3 of CCD or CMOS type;

electronic circuits 4 for generating video signals and for controlling power up, power down, image freezing, etc.;

an optical window 6, comprising a glass covering a prism 7; and a lighting system 8, comprising at least one LED.

Usually the distal part of known cameras must be covered with a transparent hygienic protection, in order to avoid patient-to-patient contamination.

When acquiring an anatomic portion with visible light, it is known that all the reflected radiation must impinge on the image sensor. On the contrary, when the anatomic portion to be acquired is lighted with a monochromatic radiation, e.g. ultraviolet, the UV radiation must excite the irradiated tissues, while the image sensor must be protected through a selective filter to receive only the weak emission emitted by stimulated tissues, without the saturation due to the reflecting exciting radiation.

Figure 2:
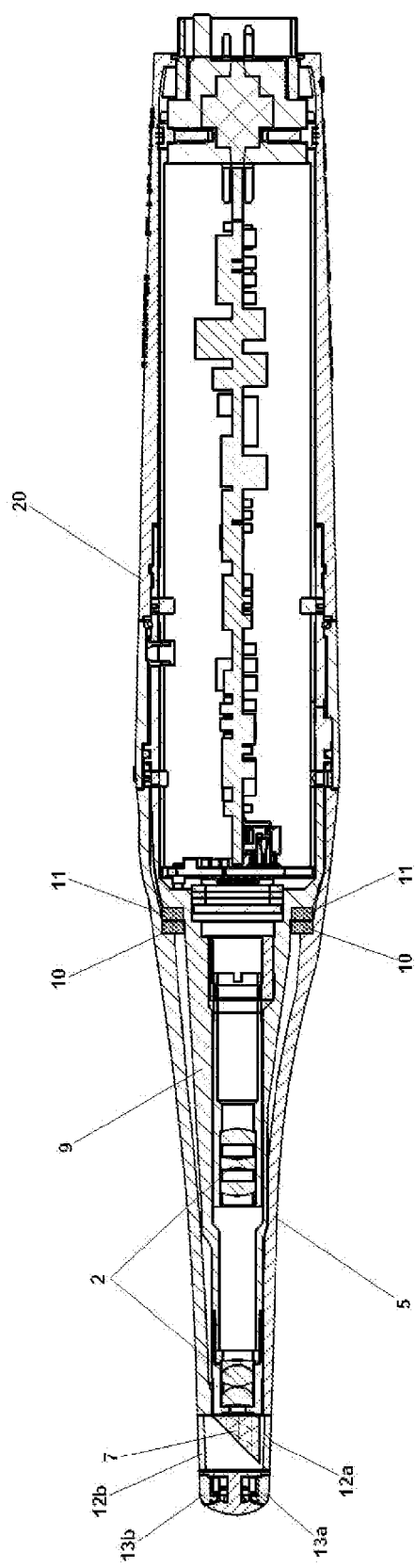
FIG. 2 Schematic longitudinal section view of a camera according to the present invention.

In a first preferred embodiment of the present invention, shown in FIG. 2, the distal part of the camera comprises: a first internal fixed part 9, integral with handgrip 20, incorporating the focusing optical system 2; an optional prism 7, when the camera is designed for lateral vision as in the typical case of dental cameras; and a magnetic tetrapolar ring 11 near the handgrip. The external part 5 is mobile, configured to rotate around fixed part 9, and comprises a second tetrapolar magnetic ring 10 in front of the corresponding ring 11 positioned on the fixed part 9. The mobile external part 5 comprises two optical windows 12a and 12b positioned on the opposed sides, and in correspondence of the optical windows 12a and 12b, two lighting systems 13a and 13b comprising one LED or a group of LEDs.

The two tetrapolar magnetic rings 10 and 11 are a magnetic embodiment of an optionally detachable connection of the mobile part 5 relative to the fixed part 9 and allow the positioning of the mobile part 5 in only two distinct fixed positions with respect to the fixed part 9, corresponding to rotations of 180° of mobile part 5, and assure their stable and precise reciprocal position. Therefore, according to the chosen rotational position, the mobile part 5 will have in front of the prism 7 the first optical window 12a, e.g. transparent to visible light and having a LED lighting system 13a irradiating white light, or the second optical system 12b, having e.g. an optical filter that is specific for a predetermined diagnostic use, and a LED lighting system 13b irradiating ultraviolet or infrared radiation.

The fixed part 9 inside the hand-piece is provided with at least two contacts for transferring the electrical connection supplying the LEDs positioned on the mobile part 5. The mobile part 5 correspondingly has sliding or spring contacts to realize the connection. This way, only the LEDs corresponding to the optical window in use are supplied. In one embodiment, additional electrical contacts can be positioned between the fixed and mobile parts, in order to enable the internal electronic circuits of the hand-piece to recognize the position of mobile part 5, and optionally to be configured appropriately.

A more general principle according to the present invention, and on which the above specific embodiment is based, consists providing means for sensing the relative angular positions or the mobile part 5 relatively to the fixed part 9. These sensing means generate a different control signal corresponding to each of at least two different discrete relative angular positions of the mobile part 5 relative to the fixed part 9, and also have the function of generating controls for automatically changing the values of the optical parameter and/or the driving parameters of the lighting system and/or the settings of the electronic circuits for image processing according to predefined values and settings. These values and settings are univocally correlated to each of the discrete relative angular positions of the mobile part and of the fixed part.

Figure 8:
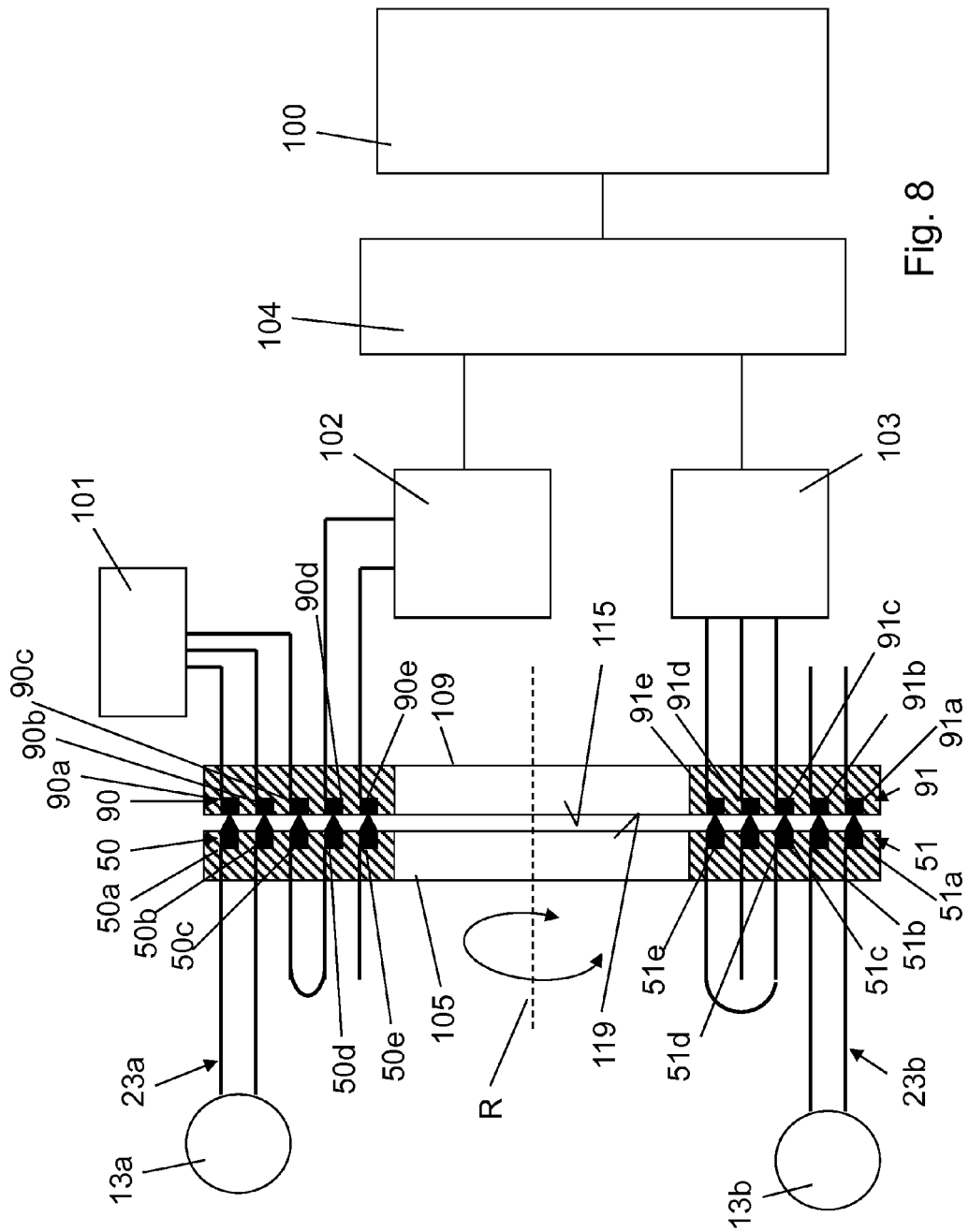
FIG. 8 A block diagram of an exemplary embodiment of the means for sensing the relative angular position between fixed part and mobile part.

FIG. 8 illustrates a block diagram related to one embodiment. In this embodiment the code is generated by an array of sensing contacts provided on the fixed part 9 in a certain angular position relative to the axis of rotation, and an array of coding contacts for each working position of the mobile part 5. The array of coding contacts on the mobile part cooperates alternatively with the sensing contact on the fixed part. Each of the coding arrays on the mobile part has a different pattern, or the contacts are connected together according to different connection schemes for each of the corresponding working positions, thus forming a univocal identification code for each of the working positions, i.e. for the corresponding relative angular position of the mobile part and the fixed part, which is read by the electronic processing unit 100 connected with the array of sensing contacts on the mobile part. This univocal code is then interpreted as a control signal for changing the settings according to the selected working position.

The sensing contacts and the coding contacts can be provided in the form of sliding contacts supported by each of two facing annular surfaces on the fixed part 9 and on the mobile part 5. These two annular surfaces carry the contacts and the contacts on at least one of the two elements 5 or 9 are biased against the facing surface of the other element, respectively 5 and 9, and thus against the contacts on the other element when the rotation brings the contacts on one surface to fall coincident with the contacts on the other surface. The contacts carrying surfaces of the mobile part 5 and the fixed part 9 can be cylindrical surfaces coaxial with the axis of rotation R of the mobile part or annular surfaces on planes perpendicular to the rotational axis and coaxial to the axis of rotation R of the mobile part. This last variant is the one illustrated in FIG. 8 and diagrammatically represented by the two rings 105 an 109 respectively on the mobile part 5 and on the fixed part 9 (which are omitted and represented by the corresponding ring 105, 109).

The facing annular frontal surfaces 115 and 119 carry at different angular positions arrays of contact arranged according to certain patterns. The patterns of contacts 50a to 50e, 51a to 51e and 90a to 90e, 91a to 91e respectively on the rotating ring 105 and on the fixed ring 109 can be linear and arranged along a circumferential path or arranged along a radial or secant path relatively to the two rings, or can be also bi-dimensional, and the contacts can be arranged according to two dimensions one circumferential and the other radial. The angular positions of the arrays of contacts on the two rings 105 and 109 are such that at certain relative angular positions, at least one of the array of contacts on the mobile ring falls coincident with at least one of the arrays of contacts on the fixed ring 109.

In its minimal embodiment, the rotating ring 105 carries two arrays of contacts 50 and 51 comprising contacts elements 50a to 50e and 51a to 51e and the ring 109 on the fixed part carries only one array of contacts elements 90 with contacts elements 90a and 90b.

In general, the arrays of contacts elements 50 and 51 on the mobile element 5 can differentiate one from the other in that some contacts may be lacking in the array and/or in that different contacts elements are shunted together in the two arrays, in order to define different codes when coming in contact with the sensing contacts elements 90a to 90e on the ring 109 of the fixed part 9. As it can be understood, the skilled person has several choice options for carrying out the coding according to this example.

According to an additional feature of the present coding means, at least an additional array 91 of sensing contacts 91a to 91e can be provided on the ring 109 of the fixed part and in such a relative angular position to the first array 90 of sensing contacts on the same ring 119 corresponding to the angular distance of two of the arrays 50, 51 of coding contacts on the ring 105 of the mobile part 5. In this situation, which is represented in FIG. 8, the second array of sensing contact 91a to 91d will be coincident with the array of coding contacts 51a to 51e, when the other array of coding contacts 50a to 50e is coincident with the first array of sensing contacts 90a to 90e, thus enabling a double position sensing of the mobile part relative to the fixed part validating the principal position information sensed by the array 90 of sensing contacts 90a to 90b. This allows overcoming by cross validation failures in the operation of the sliding contacts due, for example, to accumulation of dirt on the sliding contacts or the like, which can generate an invalid ID code or simulate an incorrect ID code for the angular position of the mobile part 5 relative to the fixed part 9. This cross validation being the more important, more angular positions are provided of the mobile part 5 relative to the fixed part 9, each representing a different working options concerning different optical parameters and/or different lighting parameters and/or different settings of the processing unit 100.

In the present example each of the contacts 50a to 50e, 51a to 51e and 90a to 90e, 91 to 91e belonging to the same array 50, 51, 90 and 91 is aligned according to a linear pattern, which in particular is on a radial direction relatively to the axis of rotation. Furthermore, in the present example, the mobile part 5 has two angular positions relatively to the fixed part 9 each one corresponding two different working options relatively to optical parameters and/or lighting parameters and/or settings of the processing unit 100. The two relative angular positions of the mobile part in relation to the fixed part 9 are at a distance of 180° one from the other, so that the contacts on the ring 105 and on the ring 109 are aligned respectively all along the same diameter.

According to the above options the ring 109 on the fixed part 9 also has two arrays 90 and 91 of contacts 90a to 90e and 91a to 91e aligned along the same diameter and at a distance of 180° one from the other so that, when as represented in FIG. 8, the coding contacts 50a to 50e are coincident with the sensing contact 90a to 90e, and at the same time the second array of coding contacts 51a to 51e on the ring 105 are coincident with the second array of sensing contacts 91a to 91e on the ring 109 of the fixed part, thereby generating position signals for cross validation of position information.

In the example of FIG. 8, which should not be understood as limiting, the mobile part 5 carries two lighting systems 13a and 13b feeding lines 23a and 23b ending at contacts respectively 50a, 50b of array 50 of coding contacts and 51a, 51b of array 51 of coding contacts. The sensing contacts 90a and 90b of array 90 are connected to a power supply 10 generating a power signal of the lighting systems. The corresponding sensing contact 91a and 91b of the second array of sensing contacts are connected to earth or zero potential. Thus, each time the coding contacts 50a, 50b or 61a, 51b fall on the sensing contacts 90a, 90b, the corresponding lighting system will be activated, while the other lighting system, whose associated contacts 50a, 50b or 51a, 51b fall coincident with the sensing contacts 91a, 91b, remains inactivated. The rotation of the mobile part 5 relative to the fixed part 9 of steps of angular displacements of 180° causes the alternative activation of one of the two sources 13a and 13b.

According to a first embodiment, means can be provided for sensing the current absorption of the lighting system and these data can be used for determining which of the two lighting systems is in use if the current absorption of the two lighting system is different one from the other. These data can be used by processing unit 100 to change some processing settings optimized for the corresponding lighting system according to predefined or preset processing protocols memorized in the processing unit 100.

As it appears from the example of FIG. 8, the arrays of coding contacts 50 and 51 and of sensing contacts are provided with further contacts respectively 50c to 50e, 51c to 51e and 90c to 90e, 91c to 91e, which are used to generate specific ID codes, which are different for each relative angular position of the mobile part 5 relative to the fixed part 9 and univocally associated to each of the different relative angular positions.

In the simple, diagrammatically shown example, the different codes are obtained by shunting together different contacts of the contacts 50c to 50e and 51c to 51e within the array 50 and 51. In FIG. 8, the coding contacts 50c and 50d in array 50 are electrically connected, while the contact 50e is isolated. In the array 51, the contacts that are connected together are the contacts 51c and 51e, while the contact 51d is isolated. Thus if a signal is active at the contacts 90c while it is read at the contacts 90d and 90e, if the signal active at 90c is read at the contact 90d the first array 50 is univocally recognized by a coding sensing unit 102, while if the signal active at 90c is read at contact 90e, the array 51 is identified as being coincident with the array 90 of sensing contacts. When, as in the example of FIG. 8, a second array of sensing contacts 91 is provided for cross validation of the data sensed by array 90 of the sensing contacts, the contact 91c to 91e are connected to a separate coding unit 103, which operates similarly to the sensing unit 102 connected to the array of sensing contacts 90.

According to the above, the two sensing units 102 and 103 reveal ID codes of two different arrays of coding contacts, which might be consistent, and if one is invalid or incorrect, then a failure signal is generated avoiding malfunctions. Consistency may, for example, be determined by a comparator or voter unit 104.

Other kinds of sensing means of the relative angular positions of the mobile part 5 relative to the fixed part can be used, for example rotational encoders or alternatively RFID tags can be positioned on the mobile part 5 at different angular positions on the annular surface 115 relative to rotation axis R. Each of the RFID tags sends a univocal ID signal, which is different from the one of the other and which is correlated to the parameters to be set when the mobile part 5 is in the relative angular position relative to the fixed part 9 corresponding to a certain working option. A RX sensor for the RFID tags is positioned at a specific angular position or at least two RX sensors are positioned at different angular positions on the fixed ring 119, so that when rotating the mobile part the relative angular position of the mobile part 5 with respect to the fixed part can be revealed by the ID signal of the RFID tag respectively falling coincident and thus communicating with the RX sensor.

In the embodiment shown in FIG. 2, switching e.g. from a working position making use of visible light 12a, 13a to a working position making use of a narrow wavelength light 12b, 13b, the circuits might be configured to activate one or the other lighting system 13a and 13b and to modify at the same time the RGB or CMY or YUV matrix of color balancing of the image sensor.

In other similar embodiments the camera might comprise hexapolar rings and be provided with distal rotating parts having three optical windows and related lighting systems, corresponding to rotational positions of 120°. For instance, the camera might comprise a first optical window transparent to visible light and surrounded by white LEDs, a second optical window transparent to visible light and surrounded by white LEDs but provided with an additional lens allowing optimal vision at a different focusing distance, and a third optical window, e.g. provided with an optical filter specific for a predetermined diagnostic use, and surrounded by ultraviolet or infrared LEDs.

In additional embodiments eight-polar magnetic rings might be used, correspondingly realizing four distinct optical windows having different features (not shown). It is also possible to use magnetic rings having a higher number of poles, and a consequent number of optical windows.

The mutual position of a couple of tetrapolar rings, and of a couple of hexapolar rings, is shown in FIG. 3. In FIG. 3, the tetrapolar rings 210 and 211 are shown in the working positions where they attract each other. The rings 310 and 311 are shown during the rotation in the position where they repel each other, providing for an easy rotation without friction. Similar considerations are applicable for rings having a higher number of poles.

The arrays of coding and sensing contacts according to the example of FIG. 8 can be modified according to different angular distances, between working positions provided for the mobile part 5 according to the embodiments having a couple of hexapolar magnetic rings or eight-polar magnetic rings.

Alternatively to the above-described preferred embodiment making use of a couple of multipolar magnetic rings, other different solutions are possible to obtain a reciprocal positioning of external mobile part 5 with respect to internal fixed part 9.

One alternative embodiment may provide mechanically rotatable connection means of the mobile part 5 in each of the different angular positions provided for the mobile part 5 relative to the fixed part, whose mechanical blocking means exercise a blocking action which can be overcome by a specific force exercised by human hands.

For instance, spring plungers may engage in suitably positioned cavities, or a system of prints may engage like a bayonet mount in suitable seats machined in the counterpart.

FIGS. 9 to 11 illustrate a first alternative of mechanical elastically releasable locking means. This means comprise a combination of at least one tooth and at least a number of notches corresponding to the number of working positions of the mobile part 5 relative to the fixed part 9, or at least one notch and at least a number of teeth corresponding to the number of working positions of the mobile part 5 relatively to the fixed part 9, or a number of teeth and a number of notches corresponding to the number of working positions of the mobile part 5 relative to the fixed part 9.

The teeth or notches are placed on a coinciding circular path coaxial with the rotation axis R of the mobile part 5 relatively to the fixed part, and are placed respectively on the mobile part and on the fixed part. Elastic means, which may also be the intrinsic elastic behavior of the material of the teeth, bias the teeth against the facing surface carrying the notches. In FIGS. 9 to 11 the rings 105 and 109, which can be the same rings carrying the coding and sensing contacts, carry on facing surfaces respectively a tooth 309 and two or more notches 305, which are arranged at different angular positions according to the angular distances provided for the different working positions of the mobile part 5 relative to the fixed part 9.

The option of having more than two positions of the notches 205 is indicated by notches in dotted lines.

FIG. 9 is a cross section according to a plane perpendicular to the surfaces of the rings 105 and 109 and coincident with the longitudinal axis of the tooth 309.

The tooth may be constructed according to different processes, In the present example the tooth 309 is obtained from the same material as the ring 109, for example a plastic material having an intrinsic elasticity and a shaped appendix obtained by cutting a window 409 in the ring 109. The tooth further has inclined surfaces 509 and 609 cooperating with correspondingly inclined surfaces 405, 505 of the notches, which facilitates the sliding movement and the displacement of the tooth out of the notches during rotation.

Figure 12:
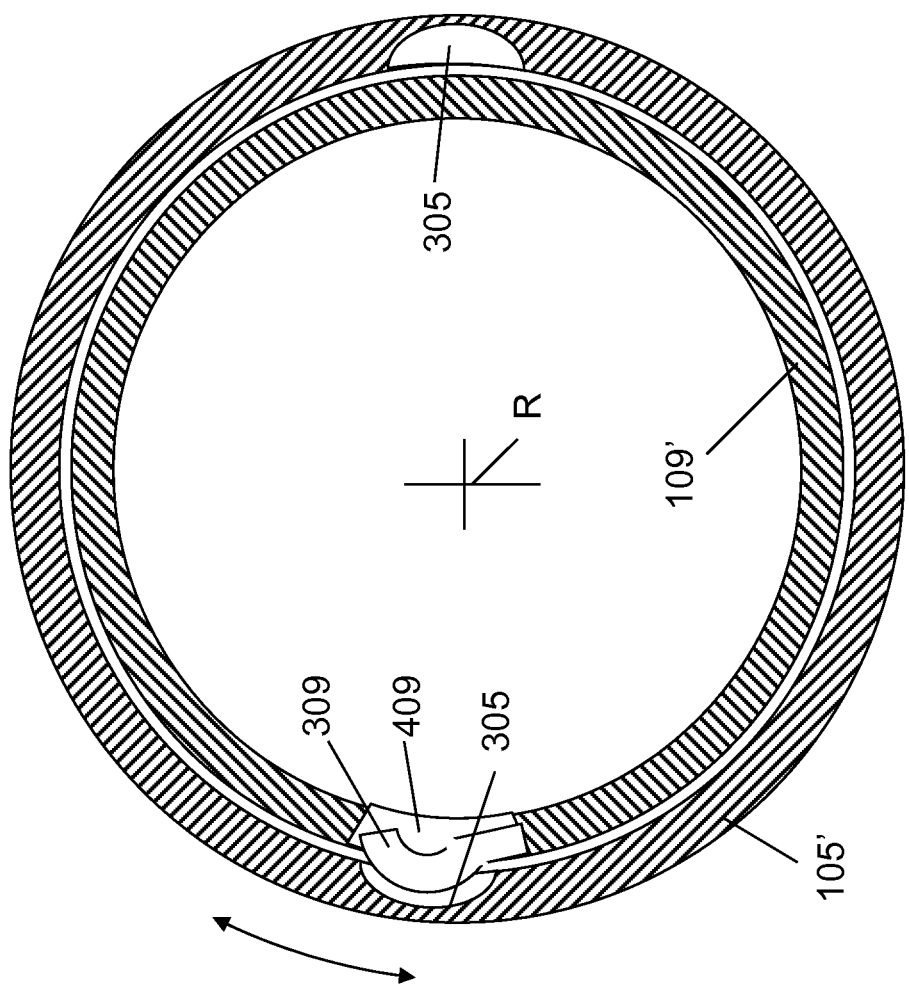
FIG. 12 A second embodiment of the mechanical releasable blocking means.

The example of FIG. 12 illustrates a similar construction of the elastic tooth cooperating with notches, which are provided on cylindrical surfaces coaxial with the axis of rotation and are positioned respectively on annular part 105' and 109' of the mobile part 5 and of the fixed part 9.

Figure 13:
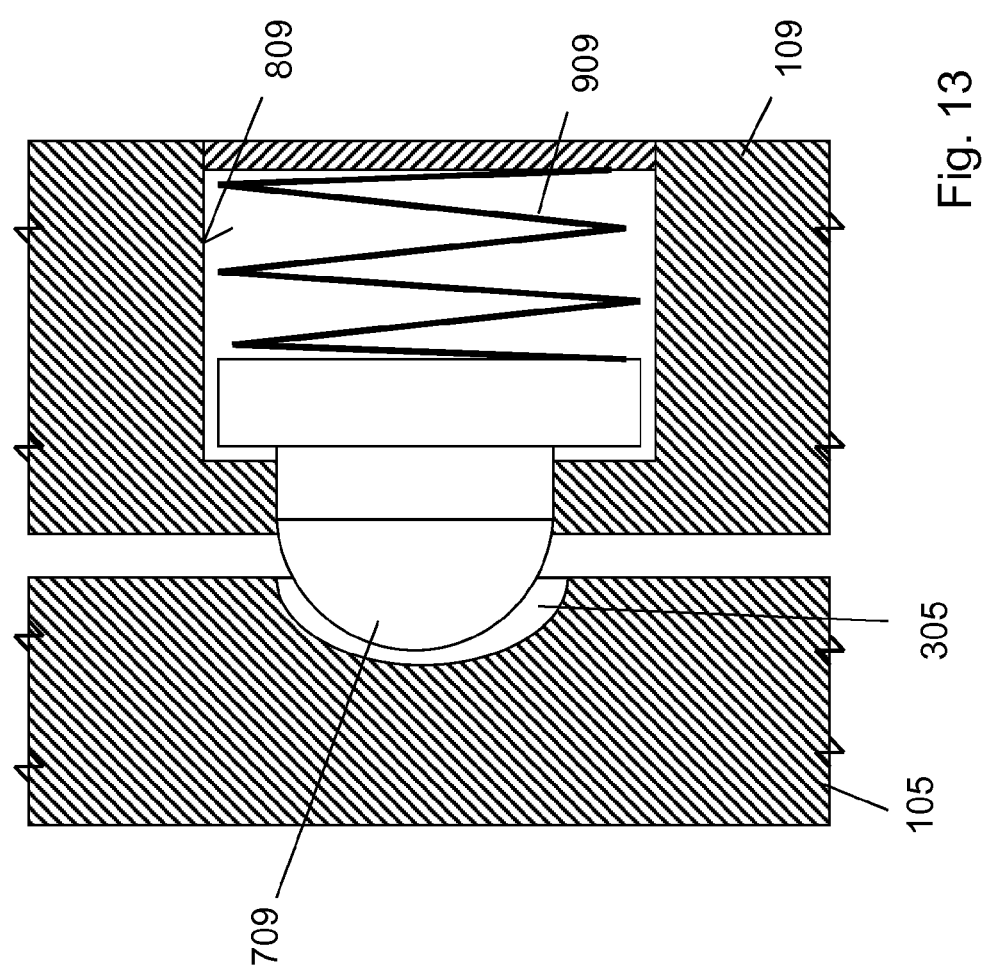
FIG. 13 An enlarged view of a mechanical releasable blocking means according to a third embodiment.

In FIG. 13 there is illustrated a simplified schematic alternative of a tooth. In this case a pin 709 is housed axially and is slideable back and forth in a seat 809 provided on the fixed part 9. A spring 909 biases the pin 709 against a facing surface on the mobile part, in which notches 305 are provided. The pin has a rounded end cooperating with a rounded notch and an enlarged end inside the seat 809 for limiting the displacement in the direction of the notch.

This construction of the tooth can be used in any combination generally described above for the releasable mechanical locking means.

Figure 4A:
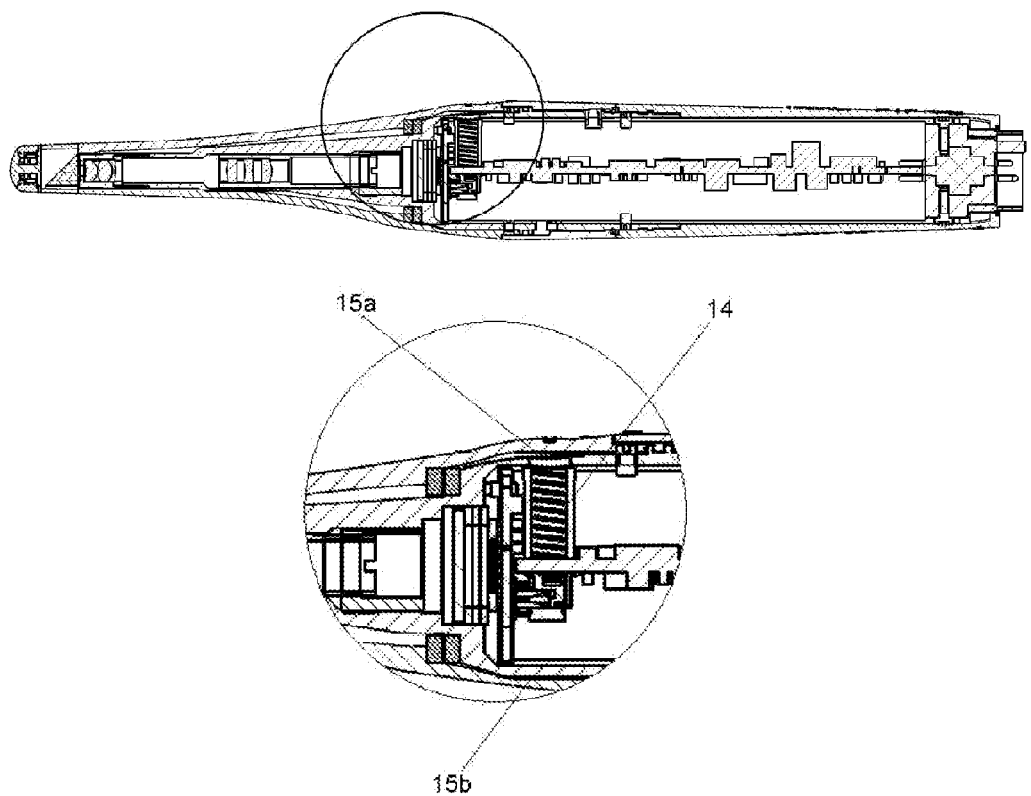
FIG. 4a Schematic longitudinal view of an embodiment having an induction supply system.
Figure 4B:
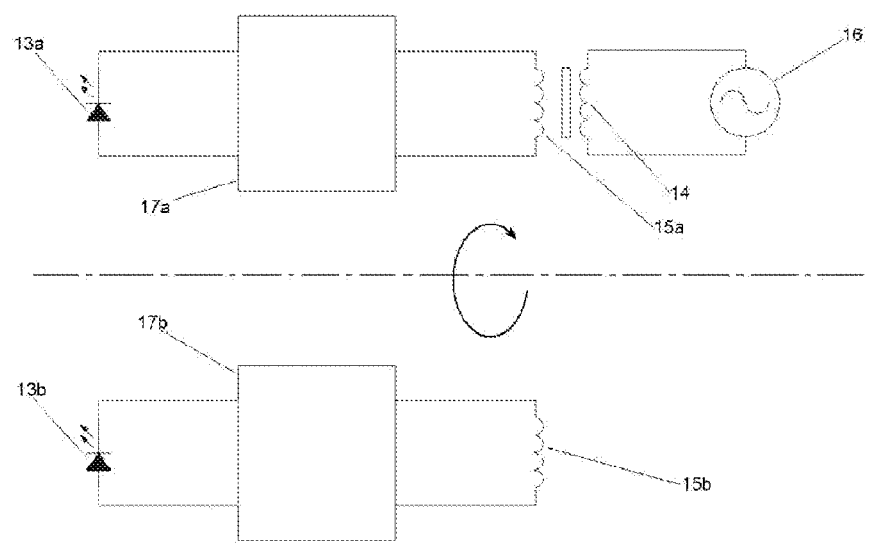
FIG. 4b Electrical schematic of the induction circuit supplying the light source.

In an alternative embodiment, shown in FIG. 4, the contacts for supplying the LEDs in the mobile part can be replaced with an induction circuit.

In the fixed part 9 and in the mobile part 5 three opposing windings 14 and 15a, 15b are provided. The winding 14, positioned in the fixed part, is controlled by a known switching circuit 16 generating a high frequency magnetic alternate flux, typically of the order of tens of kilohertz to some megahertz, and is preferably provided with a ferrite magnetic core. The two windings 15a, 15b, positioned in mobile part 5, are disposed so that in each working position only one of the two is in front of the winding 14, to get a good magnetic coupling, while the other is far from magnetic field lines and is weakly coupled, therefore not receiving a significant transfer of energy from winding 14. The two windings 15a, 15b are connected to rectifying circuits 17a, 17b of the transferred electric signal, to correctly supply one of the lighting systems 13a and 13b, due ti having winding 15a or 15b magnetically coupled with winding 14.

In this configuration, wherein electric contacts for transferring electric supply can be disposed of, it is possible to use at least a magnetic sensor in the internal fixed part 9, to which a magnet or a particular configuration of magnets is opposed in the mobile external part 5 (not shown). A further alternative is the use of a RFID (Radio Frequency IDentification) device positioned in the external mobile part 5 and of the corresponding RFID reader in the internal fixed part 9 (not shown). This last embodiment, in addition to being free of the disadvantages linked to possible oxidation or deformation of sliding contacts and of magnet demagnetization, the recognition and management of spare parts is also allowed.

Figure 5:
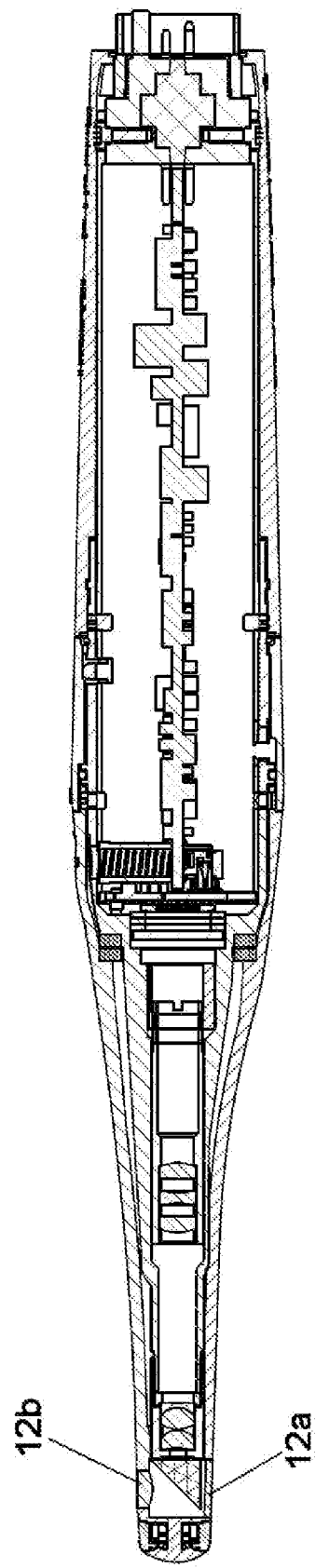
FIG. 5 Cross-sectional view of an embodiment having two optical windows for achieving two different focusing distances.

In a second preferred embodiment shown in FIG. 5, in the switching between the two working positions of the optical system, the lighting system is not changed, but the vision occurs at two different fixed focusing distances, with the same lighting source.

To obtain this function, the two optical windows 12a and 12b can be built e.g. in the following way. The optical window 12a can comprise a flat glass for the vision at a predefined distance, determined by optical system 2 only, while the optical window 12b can comprise a convex lens for the vision at a second, closer distance than the first. Alternatively (not shown) the optical window 12a can comprise a concave lens for a vision at a longer distance, and the optical window 12b can comprise a convex lens for a vision at a very close distance (macro). In this way a simplified hand-piece can be realized, from the point of view of the optical components and of the mechanical realization, which can nonetheless provide optical performances optimized for two or more (with hexapolar or eight-polar rings) working positions. This type of hand-piece can provide, at a much lower cost, optical performances comparable to those of a traditional system comprising a focusing system adjustable to pre-set positions.

Figure 6:
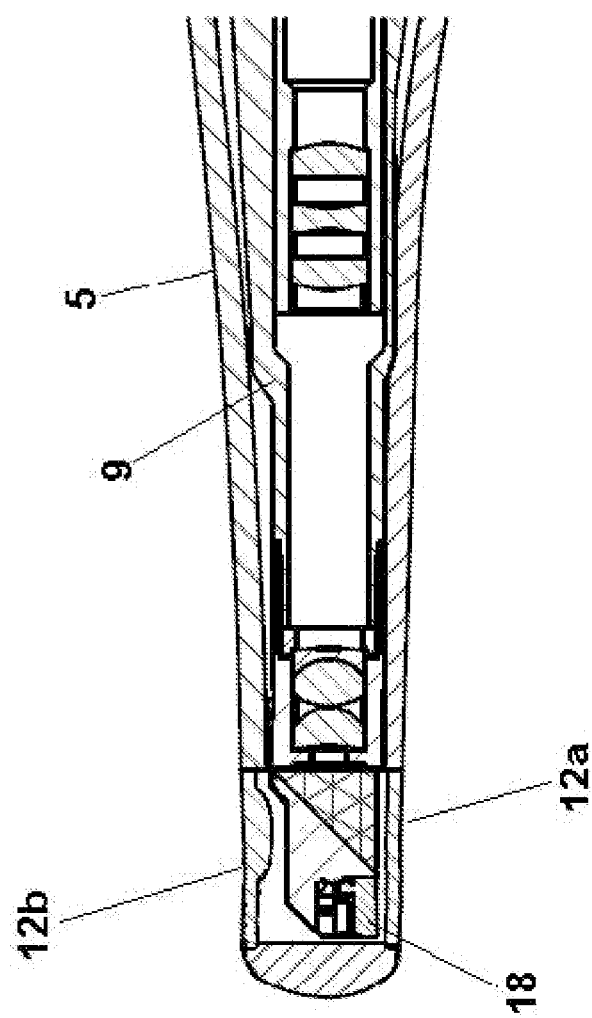
FIG. 6 Longitudinal section of a detail of the distal part of an embodiment having the light source in the fixed part.
Figure 7:
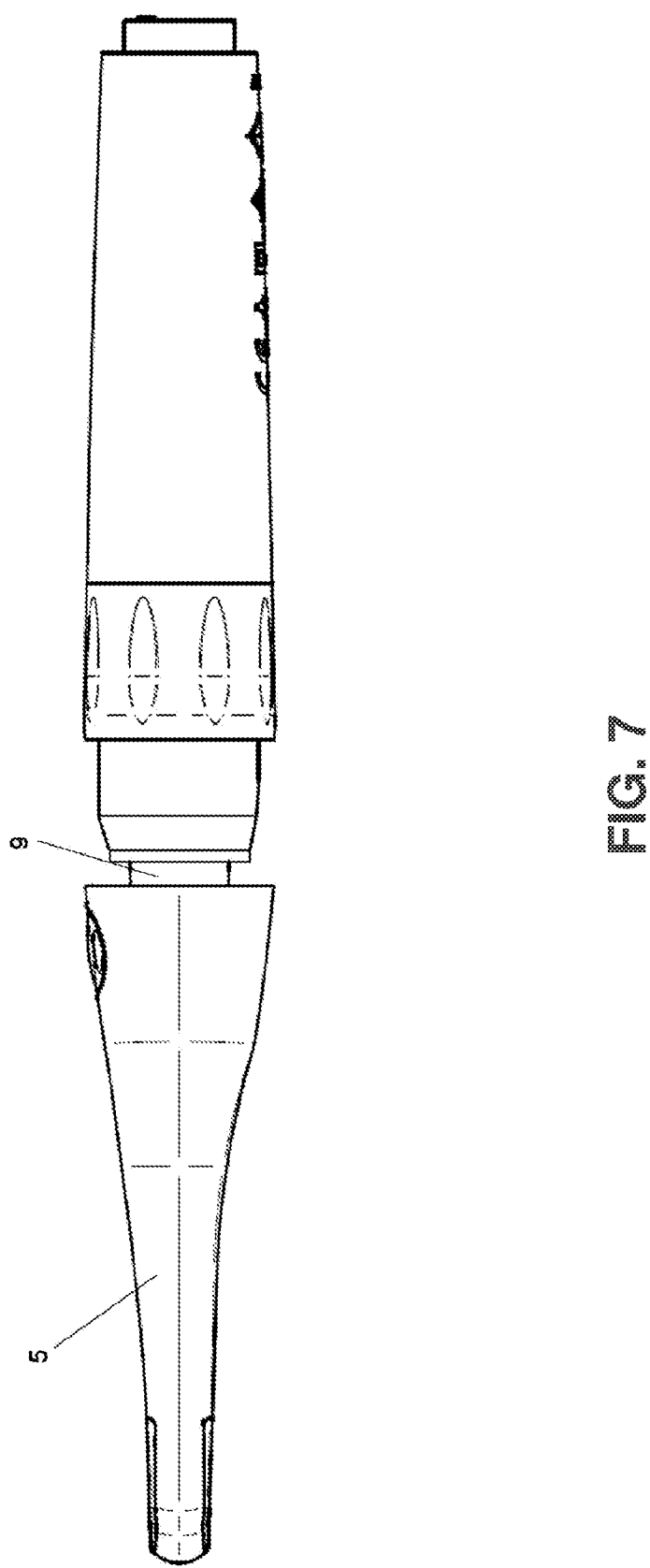
FIG. 7 Prospective view of an embodiment with removed external part.

In a third preferred embodiment, shown in detail in FIG. 6, the LED lighting system 18 can be advantageously realized directly in the internal fixed part 9 of the hand-piece tip, using also the same optical windows 12a and 12b for the lighting of the area to be acquired. The connections for the lighting system 18, being integral to fixed part 9, do not require the use of sliding contacts or induction systems, saving components and money. Because in this embodiment the external mobile part 5 does not require connections to the fixed internal part 9, it can be removed as shown in FIG. 7. The external mobile part 5, not comprising electronic parts, can be more easily cleaned, disinfected or sterilized in an autoclave. This embodiment might therefore allow dispensing of hygienic protections, which tend to worsen the acquired image quality and represent a supplementary operating cost.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become apparent to those skilled in the art and the scope of the present invention is limited only by the appended claims.

PART LIST 1. hand-piece
2. optical system
3. CCD or CMOS sensor
4. electronic circuits
5. external mobile part 6. optical window
7. prism
8. lighting system
9. internal fixed part
10. magnetic ring, mobile part
11. magnetic ring, fixed part
12a optical window
12b optical window
13a lighting system
13b lighting system
14 winding in fixed part
15 winding in mobile part
20 fixed part of the hand-piece
23a feeding line
23a feeding line
50 array of coding contacts
51 array of coding contacts
50a to 50e coding contacts
51a to 51e coding contacts
90 array of sensing contacts
91 array of sensing contacts
90a to 90e sensing contacts
91a to 91e sensing contact
105 ring
109 ring
115 annular surface
119 annular surface
305 notch
405 inclined surface
505 inclined surface
309 tooth
409 windows
509 inclined surface
609 inclined surface
709 pin
809 seat
909 spring

The invention claimed is:

1. A camera hand-piece (1) for medical use, comprising:
at least one lighting system (13a, 13b, 18);
at least one optical window (12a, 12b);
a fixed part (9) which is internal and has an optical system (2) configured to acquire images through an optical window (12a, 12b), an image sensor (3), electronic circuits (4) for image processing, optionally a prism (7);
an external part (5), which is mobile with respect to the fixed part (9) and is rotatably commutable between at least two different working positions having one or more of different optical or lighting features or settings of a processing unit that are selectable by an operator; and
a system determining a relative angular position of the mobile part relative to the fixed part, the relative angular position corresponding to each working position, the system generating for each working position a control signal automatically changing at least one of the lighting system, the settings of the processing unit, or optical parameters.

2. A camera hand-piece (1) for medical use, comprising:
at least one lighting system (13a, 13b, 18);
at least one optical window (12a, 12b);
an optical system (2) configured to acquire images through the at least one optical window (12a, 12b), the optical system including an image sensor (3);
an electronic circuit (4) for image processing, and optionally a prism (7) for deviating an optical path from the at least one optical window (12a, 12b) to the optical system (2); and
a case comprising,
a fixed part (9) housing at least the optical system (2), the image sensor (3), the electronic circuit (4), and optionally the prism (7), and
a mobile part (5), which is rotatably displaceable with respect to the fixed part (9) of the case, between different relative angular positions of the mobile and fixed parts of the case (9),
wherein:
the mobile part (5) of the case is rotatably displaceable relatively to the fixed part (9) of the case between at least two different working positions corresponding each to a specific relative angular position of the mobile part (5) relative to the fixed part (9);
each working position has optical or lighting features which are different one from the other and freely selectable by an operator; and
the mobile part (5) and the fixed part (9) are provided with a system sensing the relative angular positions and generating a different control signal corresponding to each of at least two different discrete relative angular positions, such to automatically change values of one or more of driving parameters of the lighting system or settings of the electronic circuit (4) for image processing according to predefined values and settings univocally correlated to each of the discrete relative angular positions of the mobile part (5) and of the fixed part (9).

3. The camera hand-piece according to claim 2, wherein the mobile part (5) carries at least two optical windows (12a, 12b), each optical window operating in alternative to the other and having optical parameters different from another optical window and further having different angular positions on the mobile part (5) relatively one to the other with reference to a rotation axis of the mobile part (5), each of the optical windows (12a, 12b) intersecting the optical path of the optical unit (2) and optionally of the prism (7) at one of the angular working positions of the mobile part (5) relative to the fixed part (9).

4. The camera hand-piece according to claim 1, wherein the mobile part (5) carries at least two lighting systems (13a, 13b, 18), each lightning system having optical parameters different from another lighting system and further having different angular working positions on the mobile part (5) relative one to the other with reference to a rotation axis of the mobile part (5), each of the lighting systems (13a, 13b, 18) being directed to a region to be imaged and activated at different angular working positions of the mobile part (5) relative to the fixed part (9).

5. The camera hand-piece according to claim 1, wherein a releasable blocking system is provided for releasably blocking the mobile part (5) relative to the fixed part (9) at each relative angular position corresponding to a working position, the releasable blocking system generating a releasable blocking force having an intensity set at a level that is overcome by exercising a manual rotational action on the mobile part (5) relatively to the fixed part (9).

6. The camera hand-piece according to claim 4, wherein the releasable blocking system comprises a mechanical blocking system.

7. The camera hand-piece (1) according to claim 4, wherein the mobile part (5) and the fixed part (9) are provided each with a tetrapolar magnetic ring (10, 11), and wherein working positions are commutable through a rotation of the mobile part (5) of the camera, so that magnetic rings (10, 11) couple in only two possible positions lying at 180° to each other.

8. The camera hand-piece (1) according to claim 4, wherein the angular working positions are three angular working positions lying at 120° to each other with a magnetic hexapolar ring (10), or four angular working positions lying at 90° with an eight-polar magnetic ring (10) positioned in the mobile part (5), which is in front of a corresponding ring (11) positioned in the fixed part (9).

9. The camera hand-piece (1) according to claim 8, wherein:
the at least one lighting system is at least two lighting systems (13*a*, 13*b*) positioned in the mobile part (5);
in a first working position, image acquisition occurs through a first optical window (12*a*) transparent to visible light emitted by a visible light source (13*a*), and in a second working position, the image acquisition occurs through a second optical window (12*b*) selectively transparent to an optical radiation in a predetermined wavelength band and with a narrow band monochromatic light ranging from 250 to 1200 nanometers emitted by a monochromatic source (13*b*); and
the monochromatic light is out of a transparency band of the second optical window (12*b*).

10. The camera hand-piece (1) according to claim 9, wherein the at least one lighting system (13*a*, 13*b*) for lighting a framed field is positioned in the mobile part (5) of the camera hand-piece (1), and only one lighting system (13*a* or 13*b*) is selectively supplied according to the image acquisition occurring through the first optical window (12*a*) or the second optical window (12*b*).

11. The camera hand-piece (1) according to claim 10, wherein electric supply to the at least one lighting system (13*a*, 13*b*) is provided through energy transfer via magnetic coupling of two opposed windings (14, 15).

12. The camera hand-piece (1) according to claim 1,
wherein there are at least two optical windows (12*a*, 12*b*) present in the mobile part (5), and
wherein image acquisition occurs with a visible light source (13*a*), in a first working position through a first optical window (12*a*) comprising a flat glass for an optimal vision at a first predetermined focusing distance, and in a second working position image acquisition occurs through a second optical window (12*b*) comprising a concave or convex lens allowing focusing at a second predetermined distance, different from the first predetermined focusing distance.

13. The camera hand-piece (1) according to claim 12, wherein a LED lighting system (18) for lighting a framed field is positioned in the fixed part (9) of the camera hand-piece (1).

14. The camera hand-piece (1) according to claim 13, wherein the mobile part (5) is made from parts that are not damaged at high temperatures, such to be configured to be sterilized in an autoclave.

\* \* \* \* \*